(12) United States Patent
Chiulli

(10) Patent No.: US 6,794,156 B2
(45) Date of Patent: Sep. 21, 2004

(54) CELL GROWTH, INDUCTION AND LYSIS IN AN ANTIBODY-COATED MICROPLATE FOR USE IN AN ELISA

(75) Inventor: Anthony C. Chiulli, Maynard, MA (US)

(73) Assignee: Applera Corporation, Bedford, MA (US)

( * ) Notice: Subject to any disclaimer, the term of this patent is extended or adjusted under 35 U.S.C. 154(b) by 0 days.

(21) Appl. No.: 10/124,590

(22) Filed: Apr. 18, 2002

(65) Prior Publication Data

US 2003/0008325 A1 Jan. 9, 2003

Related U.S. Application Data

(63) Continuation-in-part of application No. 09/307,797, filed on May 10, 1999, now Pat. No. 6,686,171.

(51) Int. Cl.[7] .......................... A61K 51/00; G01N 33/53; G01N 33/542; G01N 33/537; G01N 33/543
(52) U.S. Cl. .................. 435/7.93; 435/7.1; 435/7.71; 435/7.72; 435/7.9; 435/7.91; 435/7.92; 435/7.93; 435/7.94; 435/7.95; 435/21; 435/39; 435/41; 435/69.1; 435/69.3; 435/174; 435/176; 435/243; 436/512; 436/513
(58) Field of Search ................. 435/4.71, 7.2, 435/7.37, 7.4, 7.6, 7.92, 7.93, 7.94, 7.95, 21, 41, 69.3, 174, 181, 183, 333, 338

(56) References Cited

U.S. PATENT DOCUMENTS

| | | |
|---|---|---|
| 4,115,538 A | 9/1978 | Satoh et al. |
| 4,931,569 A | 6/1990 | Edwards et al. |
| 4,962,192 A | 10/1990 | Schaap |
| 5,089,424 A * | 2/1992 | Khali et al. .................. 436/518 |
| 5,112,960 A * | 5/1992 | Bronstein et al. .......... 536/18.1 |
| 5,145,772 A * | 9/1992 | Voyta et al. ................... 435/4 |
| 5,336,595 A | 8/1994 | Strader et al. |
| 5,399,500 A | 3/1995 | Oppenheimer et al. |
| 5,547,836 A * | 8/1996 | Bronstein et al. .............. 435/6 |
| 5,654,154 A | 8/1997 | Bronstein et al. .............. 435/6 |
| 5,739,001 A * | 4/1998 | Brown et al. .............. 435/7.93 |

OTHER PUBLICATIONS

Chiulli, et al., "A Novel High Throughput Chemiluminescent Assay for the Measurement of Cellular Cyclic Adenosine Monophosphate Levels", Journal of Biomolecular Screening, 5, 4, 239–247 (2000).

* cited by examiner

*Primary Examiner*—Nita Minnifield
*Assistant Examiner*—J. Hines
(74) *Attorney, Agent, or Firm*—Piper Rudnick LLP; Steven B. Kelber

(57) ABSTRACT

A competitive assay to determine the presence and concentration of an intracellular analyte (e.g., cAMP) in a sample is provided. All of the steps of the assay can be performed on the same assay plate, thereby eliminating the need to transfer the cells from a tissue culture plate on which the cells are grown, induced and lysed to a separate assay plate. The assay procedure includes combining, in a reaction chamber provided with a capture antibody, an antibody for the analyte, the sample to be assayed, and a conjugate of the analyte and an enzyme such as alkaline phosphatase. The mixture is incubated and washed and an enzyme labile substrate (e.g., a chemiluminescent, fluorescent or calorimetric substrate) is added. The assay can also be performed with a tagged analyte (e.g., an analyte having a radioactive or fluorescent tag) instead of an enzyme conjugate.

22 Claims, 15 Drawing Sheets

| cAMP, pm/well | Nonshake | Shake | Ratios | S/0 Nonshake | S/0 Shake |
|---|---|---|---|---|---|
| 60000 | 766.1 | 777.75 | 0/0.0006 | 0.916 | 0.962 |
| 6000 | 835.1 | 737.13 | 0/0.006 | 0.960 | 0.967 |
| 600 | 2172.9 | 2495.75 | 0/0.06 | 0.839 | 1.040 |
| 60 | 10780.4 | 13790.75 | 0/0.6 | 0.923 | 1.452 |
| 6 | 37330.3 | 63098.63 | 0/6 | 1.477 | 3.586 |
| 0.6 | 59693.9 | 155820.25 | 0/60 | 5.113 | 16.407 |
| 0.06 | 65697.0 | 217485.25 | 0/600 | 25.369 | 90.661 |
| 0.006 | 57404.8 | 233952.50 | 0/6000 | 66.008 | 306.959 |
| 0.0006 | 60196.8 | 235253.75 | 0/60000 | 71.959 | 290.925 |
| | 55124.6 | 226267.06 | | | |

FIG. 2B

| Vendor | Technology | Methodology | Format | Acetylated Sensitivity | Acetylated Dynamic Range | Non-Acetylated Sensitivity | Non-Acetylated Dynamic Range |
|---|---|---|---|---|---|---|---|
| ABI-Tropix | cAMP-Screen™ | Chemiluminescent ELISA | 96-well | NA | NA | 0.005 pmol/well | 0.006 to 6,000 pmol/well |
|  |  |  | 384-well | NA | NA | 0.005 pmol/well | 0.02 to 2,000 pmol/well |
| Amersham | BIOTRAK™ SPA | Radioactivity | 96-well | NA | NA | 0.1 pmol/well | 0.2 to 12.8 pmol/well |
|  |  |  | Tube | 0.001 pmol/tube | 0.002 to 0.128 pmol/tube | 0.0135 pmol/tube | 0.025 to 1.6 pmol/tube |
| IGEN | ORIGEN | Electrochemiluminescence | 96-well | NA | 0.075 to 19 pmol/sample | NA | NA |
| Assay Design | Correlate-EIA | Colorimetric | 96-well | 3.7 fmol/well | 0.78-20 pmol/ml | 39 fmol/well | 0.78 -200 pmol/ml |
| Molecular Devices Corporation | FP (LJL) CatchPoint | Fluorescent Polarization Fluorescent ELISA | 384-well | NA | NA | .6pmol/well | 0.1 to 500 pmol/well |
|  |  |  | 384-well | NA | NA | 0.006 pmol/well | 0.01 to 4.8 pmol/well |
| Perkin-Elmer | ALPHAScreen™ | LOCI | 384-well | NA | NA | NA | 0.01 to 1 pmol/well |
|  | FLASHPLATE® | Radioactivity | 96-well | NA | .025 to 2 pmol/well | 0.2 pmol/well | 0.5 to 50 pmol/well |
|  | HTRF® | Delfia | 96-well | 0.5 pg/ml | 14-910 fmol/liter | NA | NA |
|  |  |  | 384-well | 0.28 pmol/well | 0.2 - 100 pmol/well | NA | NA |

FIG. 5

| pmol/well | TR717™ 1 second RLU | NorthStar™ 60 second ADU | NorthStar™ 60 second Normalized | Ratio | TR717™ 1 second RLU | NorthStar™ 60 second ADU |
|---|---|---|---|---|---|---|
| 0 | 189261 | 43671.7 | 191359.1 | 0/0.006 | 1.12 | 1.12 |
| 0.006 | 168326 | 39123.3 | 171429.1 | 0.006/0.06 | 1.18 | 1.19 |
| 0.06 | 142821.5 | 32837.65 | 143886.8 | 0.06/0.6 | 1.87 | 1.89 |
| 0.6 | 76363.5 | 17342.65 | 75991.4 | 0.6/6 | 4.25 | 4.44 |
| 6 | 17988.5 | 3902.5 | 17099.8 | 6/60 | 3.34 | 3.33 |
| 60 | 5391 | 1172.55 | 5137.8 | 60/600 | 3.68 | 3.58 |
| 600 | 1465.5 | 327.15 | 1433.5 | 600/6000 | 1.54 | 1.51 |
| 6,000 | 951.5 | 217.15 | 951.5 | 0/6000 | 198.91 | 201.11 |

| NPY | Basal | | 1 uM | | Isoproterenol 10 uM | | 100 uM | | Basal | | 1 uM | | Forskolin 10 uM | | 100 uM | | Basal | |
|---|---|---|---|---|---|---|---|---|---|---|---|---|---|---|---|---|---|---|
| | 7 | 8 | 9 | 10 | 11 | 12 | 13 | 14 | 15 | 16 | 17 | 18 | 19 | 20 | 21 | 22 | 23 | 24 |
| 0 | 28203 | 29219 | 4613 | 4795 | 4177 | 4408 | 4000 | 4286 | 27807 | 24012 | 4297 | 3602 | 2519 | 2608 | 1540 | 2251 | 24317 | 27997 |
| 1nM | 29098 | 29729 | 4414 | 4135 | 4346 | 4291 | 4015 | 4543 | 27029 | 27110 | 4043 | 4219 | 3150 | 3070 | 1959 | 2175 | 23850 | 26042 |
| | 26159 | 27632 | 5006 | 4896 | 4693 | 4853 | 4966 | 4825 | 26000 | 29127 | 4801 | 4984 | 2481 | 2792 | 1825 | 2159 | 24297 | 23903 |
| 10nM | 28231 | 28251 | 5407 | 5133 | 5307 | 6124 | 5602 | 6256 | 26194 | 29963 | 6493 | 5735 | 3252 | 3253 | 1952 | 2228 | 25453 | 24820 |
| | 25992 | 26207 | 6847 | 6427 | 6052 | 6389 | 7739 | 6881 | 28372 | 27169 | 6238 | 7474 | 3500 | 3438 | 2048 | 2171 | 28228 | 29197 |
| | 29888 | 27745 | 7421 | 6355 | 6709 | 7014 | 8397 | 7840 | 24339 | 26940 | 7929 | 8154 | 4787 | 4794 | 2436 | 2680 | 29026 | 30553 |
| 100nM | 28923 | 30749 | 11842 | 8489 | 7854 | 7908 | 8562 | 8052 | 22718 | 24667 | 9132 | 11101 | 5299 | 4159 | 2789 | 2899 | 30061 | 31522 |
| | 31456 | 31233 | 6582 | 7709 | 7896 | 8896 | 8944 | 7599 | 23493 | 23150 | 11505 | 11710 | 5767 | 5342 | 3101 | 3211 | 31820 | 26064 |

FIG. 7A

Average RLU (each data point is n=4)

| Basal | Isoproterenol | | | Forskolin | | | Basal | Average Total Basal | NPY |
|---|---|---|---|---|---|---|---|---|---|
| | 1uM | 10uM | 100uM | | 1uM | 10uM | 100uM | | |
| 29062 | 4489 | 4306 | 4211 | 26490 | 4040 | 2837 | 1981 | 25552 | 27034 | 0 |
| 27818 | 5111 | 5244 | 5412 | 27821 | 5503 | 2945 | 2041 | 24618 | 26753 | 1nM |
| 27408 | 6763 | 8541 | 7664 | 26705 | 7449 | 4130 | 2271 | 28987 | 27700 | 10nM |
| 33090 | 8643 | 7759 | 8184 | 23510 | 10900 | 5452 | 3043 | 30689 | 29097 | 100nM |

Average RLU S/N

| Basal/Isoproterenol | | | Basal/Forskolin | | |
|---|---|---|---|---|---|
| 1uM | 10uM | 100uM | 1uM | 10uM | 100uM |
| 6.0 | 6.3 | 6.4 | 6.7 | 9.5 | 13.6 |
| 5.2 | 5.1 | 4.9 | 4.9 | 9.1 | 13.1 |
| 4.1 | 4.2 | 3.8 | 3.7 | 6.7 | 12.2 |
| 3.4 | 3.8 | 3.6 | 2.7 | 5.3 | 9.6 |

FIG. 7B

Average pmol/well (each data point is n=4)

| | Isoproterenol | | | | Forskolin | | | Average Total |
|---|---|---|---|---|---|---|---|---|
| Basal | 1uM | 10uM | 100uM | Basal | 1uM | 10uM | 100uM | Basal |
| 6.0 | 220 | 228 | 229 | 8.7 | 235 | 280 | 318 | 10.0 | 8.2 |
| 7.2 | 201 | 197 | 192 | 7.2 | 190 | 276 | 315 | 11.5 | 8.6 |
| 7.6 | 158 | 163 | 138 | 8.4 | 143 | 232 | 305 | 6.0 | 7.4 |
| 8.8 | 120 | 136 | 128 | 10.5 | 86 | 191 | 272 | 4.7 | 7.2 |

Average pmol/well S/N

| | Isoproterenol/Basal | | | Forskolin/Basal | | | NPY |
|---|---|---|---|---|---|---|---|
| 1uM | 10uM | 100uM | 1uM | 10uM | 100uM | |
| 26.7 | 27.5 | 27.8 | 26.5 | 34.1 | 38.6 | 0 |
| 23.3 | 22.9 | 22.3 | 22.0 | 32.1 | 36.6 | 1nM |
| 21.4 | 22.1 | 18.7 | 19.3 | 31.5 | 41.3 | 10nM |
| 16.7 | 19.0 | 17.9 | 12.0 | 26.8 | 37.9 | 100nM |

FIG. 7C

| NPY | Basal | | Isoproterenol | | | | | | | | Basal | | 1 uM | | Forskolin | | 100 uM | | Basal | |
| | 7 | 8 | 1 uM | | 10 uM | | 100 uM | | | | 15 | 16 | 17 | 18 | 10 uM | | 21 | 22 | 23 | 24 |
| | | | 9 | 10 | 11 | 12 | 13 | 14 | | | | | | | 19 | 20 | | | | |
|---|---|---|---|---|---|---|---|---|---|---|---|---|---|---|---|---|---|---|---|---|
| 0 | 45460 | 43529 | 8305 | 8526 | 9102 | 11739 | 8024 | 10101 | | | 41928 | 48278 | 8094 | 11535 | 4863 | 6624 | 3786 | 4403 | 53368 | 67315 |
| | 49438 | 38217 | 9948 | 8401 | 8602 | 8539 | 9658 | 9971 | | | 49966 | 43693 | 8685 | 10029 | 6756 | 6386 | 4009 | 4504 | 58186 | 66175 |
| 1nM | 41449 | 39767 | 10918 | 10693 | 9045 | 10811 | 10247 | 11421 | | | 35425 | 35751 | 11594 | 14671 | 7329 | 8323 | 4007 | 4325 | 39082 | 62947 |
| | 46750 | 42554 | 11994 | 11645 | 11516 | 11763 | 13536 | 11259 | | | 46990 | 42854 | 12025 | 13431 | 8610 | 9596 | 5746 | 4595 | 42455 | 64699 |
| 10nM | 37927 | 41090 | 11050 | 12068 | 8931 | 11606 | 12013 | 14358 | | | 35596 | 39158 | 12150 | 14303 | 7912 | 10186 | 4222 | 5311 | 31808 | 64329 |
| | 42114 | 39549 | 14775 | 11940 | 12595 | 11541 | 14002 | 13916 | | | 44266 | 42792 | 16430 | 16372 | 12060 | 11576 | 6805 | 6507 | 37683 | 60167 |
| 100nM | 33324 | 34903 | 9624 | 12077 | 10515 | 12282 | 11958 | 14881 | | | 32314 | 40782 | 12307 | 13392 | 8968 | 9593 | 5299 | 6816 | 39682 | 58753 |
| | 37703 | 38204 | 11887 | 11243 | 13228 | 14323 | 14971 | 12491 | | | 36339 | 43374 | 18592 | 21235 | 10564 | 14149 | 7801 | 8704 | 50426 | 69403 |

FIG. 8A

Average RLU (each data point is n=4)

| | Isoproterenol | | | | Forskolin | | | | Average Total Basal | NPY |
|---|---|---|---|---|---|---|---|---|---|---|
| Basal | 1uM | 10uM | 100uM | Basal | 1uM | 10uM | 100uM | Basal | | |
| 44161 | 8795 | 9496 | 9439 | 45966 | 9586 | 6157 | 4176 | 61261 | 50463 | 0 |
| 42630 | 11313 | 10784 | 11616 | 40255 | 12930 | 8465 | 4668 | 52296 | 45060 | 1nM |
| 40170 | 12459 | 11168 | 13572 | 40453 | 14814 | 10434 | 5711 | 48497 | 43040 | 10nM |
| 36034 | 14208 | 12587 | 13575 | 38202 | 15882 | 10818 | 7154 | 57067 | 43767 | 100nM |

Average RLU S/N

| Basal/Isoproterenol | | | | Basal/Forskolin | | | |
|---|---|---|---|---|---|---|---|
| 1uM | 10uM | 100uM | | 1uM | 10uM | 100uM | |
| 5.7 | 5.3 | 5.3 | | 5.3 | 8.2 | 12.1 | |
| 4.0 | 4.2 | 3.9 | | 3.5 | 5.3 | 9.7 | |
| 3.5 | 3.9 | 3.2 | | 2.9 | 4.1 | 7.5 | |
| 3.9 | 3.5 | 3.2 | | 2.8 | 4.0 | 6.1 | |

FIG. 8B

Average pmol/well (each data point is n=4)

| Basal | Isoproterenol 1uM | 10uM | 100uM | Basal | Forskolin 1uM | 10uM | 100uM | Basal | Average Total Basal | NPY |
|---|---|---|---|---|---|---|---|---|---|---|
| 0.6 | 73 | 67 | 67 | 0.5 | 66 | 105 | 137 | 0.1 | 0.4 | 0 |
| 0.7 | 52 | 56 | 50 | 1.0 | 42 | 77 | 128 | 0.2 | 0.7 | 1nM |
| 1.0 | 45 | 53 | 38 | 1.0 | 32 | 59 | 111 | 0.3 | 0.8 | 10nM |
| 1.8 | 53 | 44 | 38 | 1.4 | 28 | 56 | 92 | 0.1 | 1.1 | 100nM |

Average pmol/well S/N

| Isoproterenol/Basal | | | Forskolin/Basal | | | NPY |
|---|---|---|---|---|---|---|
| 1uM | 10uM | 100uM | 1uM | 10uM | 100uM | |
| 194.2 | 176.6 | 178.0 | 174.4 | 277.8 | 363.6 | 0 |
| 79.6 | 85.5 | 78.3 | 63.9 | 117.1 | 196.1 | 1nM |
| 56.5 | 67.4 | 48.6 | 41.1 | 74.4 | 141.3 | 10nM |
| 48.4 | 40.2 | 35.1 | 25.7 | 51.1 | 84.0 | 100nM |

FIG. 8C

CELL GROWTH, INDUCTION AND LYSIS IN AN ANTIBODY-COATED MICROPLATE FOR USE IN AN ELISA

CROSS-REFERENCE TO RELATED APPLICATIONS

This application is a continuation-in-part of U.S. patent application Ser. No. 09/307,797, which was filed on May 10, 1999 now U.S. Pat. No. 6,686,171.

BACKGROUND OF THE INVENTION

1. Field of the Invention

This invention relates generally to a competitive chemiluminescent assay for the detection of the presence of an analyte in a sample. More specifically, the present invention relates to a competitive assay for determining the concentration of an analyte (e.g., a cyclic nucleotide monophosphate such as cAMP) in a sample comprising cells wherein the cells are grown on an antibody coated plate.

2. Discussion of the Background

A wide variety of metabolic responses are keyed to release of intracellular cyclic adenosine monophospate (cAMP). In many cases, these responses are mediated by cAMP-dependent protein kinase which, in the presence of elevated cAMP levels, triggers a wide variety of activating reactions. Among the best known metabolic responses keyed to cAMP are the conversion of glycogen to glucose in the liver, as well as a variety of activities keyed to the glycogen/glucose energy cycle. The principle hormone in this cycle that induces a rise in cAMP is epinephrine. There are, however, a wide variety of other hormones that will also trigger cAMP release, which in turn keys a metabolic response mediated by the kinase. These include adrenocorticotropic hormone (ACTH), follicle-stimulating hormone (FSH), luteinizing hormone (LH), thyroid-stimulating hormone (TSH), parathyroid hormone, vasopressin and prostaglandin I. Accordingly, it is clear that cAMP levels in specific tissues of mammals, including humans, may be key indicators of a variety of hormonal functions and interactions.

cAMP is only the best known of the cyclic nucleotides. In general, cyclic nucleotides appear as monophosphates. Guanosine monophosphate (cGMP), uridine monophosphate (cUMP) and cytidine monophosphate (cCMP) may all importantly bear on a wide variety of hormonal functions and intercellular interactions that may be desirably measured. cAMP is the most studied of these "messenger" cyclic nucleotides.

Assays, including competitive ELISA assays, for cAMP are known. A widely reported assay is available from Assay Design and is a colorimetric assay. Other immunoassay products are available from Amersham Biosciences, (a scintillation proximity assay), Perkin-Elmer (FLASHPLATE®, ALPHAScreen™, fluorescent polarization) as well as IGEN (electrochemiluminescence). The Assay Design embodiment employs assay kits (also available under the trademark BIOMOL™) in a classic example of a competitive ELISA assay, in which the strength of the signal is inversely proportional to the concentration of the cyclic nucleotide present. The kit from Assay Design is for measurement of light absorption. A fluorescent assay kit is available from Molecular Devices.

Because of the very low values of cyclic nucleotides that may need to be detected in a variety of tissue samples, high sensitivity is often required. Many of the commercially available assays for cAMP itself do not offer this sensitivity and, therefore, require acetylation of the cAMP to promote better antibody binding for greater sensitivity. It would therefore be desirable to improve the sensitivity of cAMP assays. Such heightened sensitivity would be especially useful in assays for determining the effect of G proteins (e.g., $G_I$ and $G_S$ proteins) on cAMP levels. Such assays could be useful to help elucidate signal transduction mechanisms.

In addition, conventional assays are very expensive, due in part to the numerous steps necessary to complete them. Therefore, a need also exists for assays that require fewer steps and are therefore easier to automate and less expensive to run.

Accordingly, it remains a goal of those of skill in the art to find a competitive immunoassay that requires fewer steps and that is highly sensitive, offers a broad dynamic range, and employs reagents that can be obtained through simplified procedures.

SUMMARY OF THE INVENTION

According to a first aspect of the invention, a competitive immunoassay for detecting the amount of an analyte in a sample comprising cells is provided. The immunoassay includes steps of: providing an assay plate comprising one or more wells, wherein the wells are coated with a capture antibody; adding the sample to the one or more wells; growing the cells of the sample in the one or more wells; lysing the cells in the one or more wells; combining with the cell lysates in the one or more wells, (1) a conjugate of the analyte and an enzyme and (2) a primary antibody that is bound by the capture antibody and that binds, when so bound, the analyte to form a reaction mixture; incubating the reaction mixture to permit binding of the primary antibody and the conjugate; washing the reaction mixture to remove unbound conjugate or antibody; adding to the reaction mixture in the one or more wells a substrate comprising an enzyme labile group, wherein the enzyme of the conjugate is capable of cleaving the enzyme labile group of the substrate; and measuring a signal resulting from the cleavage of the enzyme labile group. The signal can be used to determine the presence and/or the concentration of the analyte in the sample. The analyte can be a cyclic nucleotide phosphate such as cyclic adenosine monophosphate (cAMP), cyclic guanosine monophosphate (cGMP), cyclic uridine monophosphate (cUMP) or cyclic cytidine monophosphate (cCMP). The enzyme can be alkaline phosphatase. The substrate can be a chemiluminescent substrate, a fluorescent substrate or a calorimetric substrate. Preferably, the substrate is a chemiluminescent 1,2-dioxetane substrate.

According to a second aspect of the invention, a competitive immunoassay for detecting the amount of an analyte in a sample comprising cells is provided. The immunoassay includes steps of: providing an assay plate comprising one or more wells, wherein the wells are coated with a capture antibody; adding the sample to the one or more wells; growing the cells of the sample in the one or more wells; lysing the cells in the one or more wells; combining with the cell lysate in the one or more wells, (1) a tagged analyte and (2) a primary antibody that is bound by the capture antibody and that binds, when so bound, the analyte to form a reaction mixture; incubating the reaction mixture to permit binding of the primary antibody and the tagged analyte; washing the reaction mixture to remove unbound tagged analyte or antibody; and detecting a signal from the tagged analyte remaining in the one or more wells. The signal can be used to determine the presence and/or the concentration of the analyte in the sample. The analyte can be modified with an enzyme, or tagged with a fluorescent or a radioactive tag.

BRIEF DESCRIPTION OF THE DRAWINGS

FIGS. 2A and 2B provide a graphic illustration and tabular data comparing the signal obtained by shaking the reaction mixture and not shaking the reaction mixture during the incubation period.

FIG. 5 is a table comparing sensitivity and dynamic range of the claimed invention with other commercial assays for cAMP.

FIGS. 6A and 6B show a graphic illustration and tabular data comparing luminescence data obtained from two different luminometers according to the present invention.

FIGS. 7A–7C are tables presenting the data obtained from an assay according to the present invention wherein cells are grown, treated with agonists, lysed, and assayed all in the wells of a clear bottom assay capture plate.

FIGS. 8A–8C are tables presenting the data obtained from a conventional assay wherein cells are grown, treated with agonists, and lysed in a standard tissue culture plate and the cell lysate is then transferred to a solid-bottom assay capture plate for the assay.

DETAILED DESCRIPTION OF THE INVENTION

Figure 1:
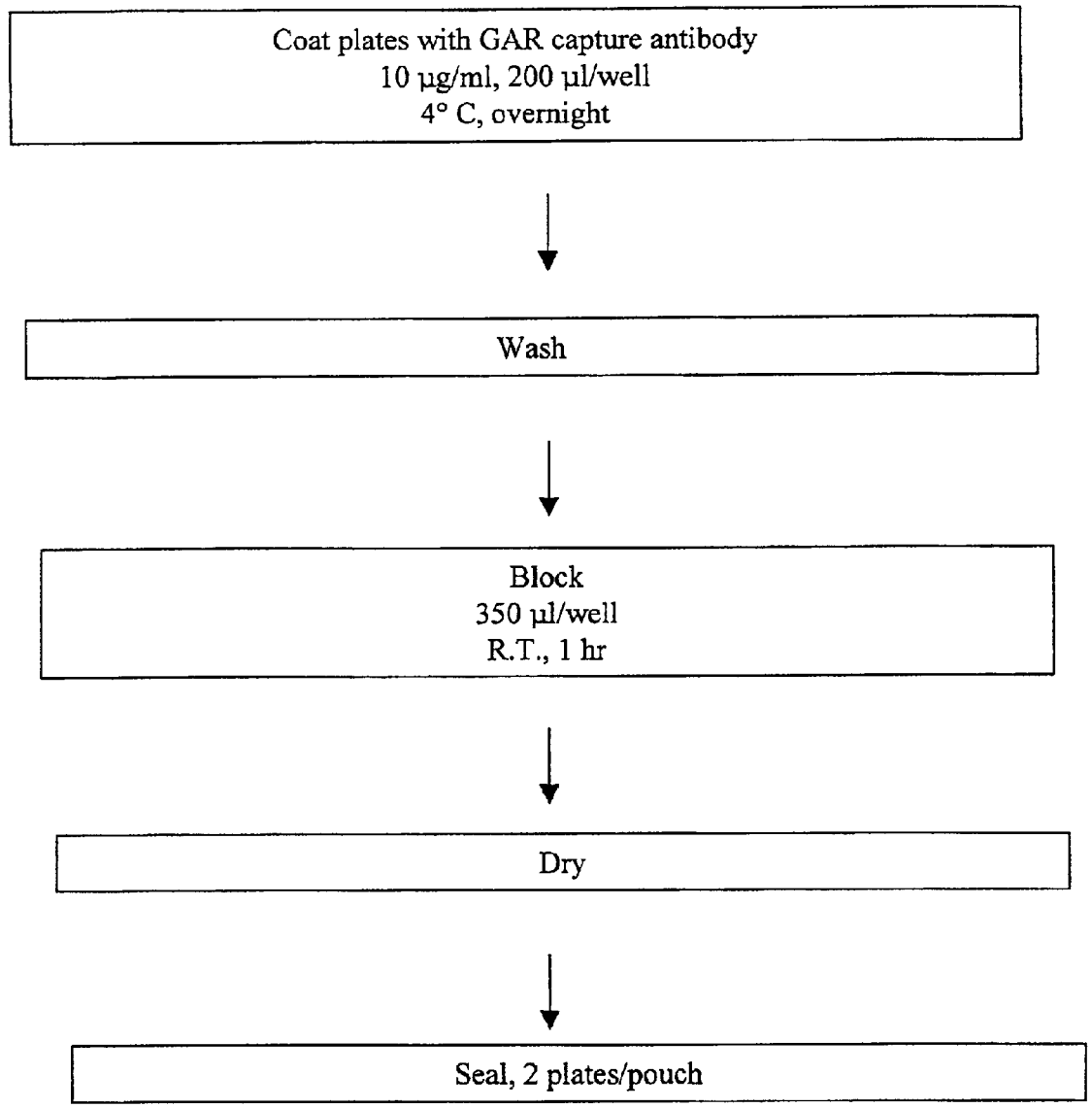
FIG. 1 is a flowchart illustrating the method of manufacturing the coated plates ("reaction chambers") of the invention.

The above objects, and others discussed in more detail below, are met by a chemiluminescent, competitive ELISA assay that relies on the high chemiluminescent sensitivity of 1,2-dioxetanes. These dioxetanes are the subject of numerous U.S. patents. The 1,2-dioxetanes that are useful in the claimed invention typically have a generic structure of Formula I:

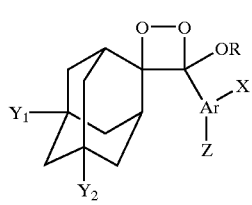

(I)

In Formula I, $Y_1$, $Y_2$ and X are variously electron-active moieties, in that they are either electron donating or electron withdrawing. Exemplary groups include halogens, particularly chlorine; alkoxy groups, particularly methoxy; amines; alkyls; etc. In the alternative, these groups are hydrogen. Any one or more of $Y_1$, $Y_2$ or X may be other than hydrogen, or they may all be hydrogen. Substituent R is an alkyl, aralkyl, cyclic alkyl or heteroalkyl comprising an O, N, P or S moiety, in general of less than 20 carbon atoms. Desirably, R is alkyl. R may be substituted with groups intended to enhance solubility, as well as reactivity, which may include halogen substituents such as one or more fluorine atoms, carboxy (COO) substituents, sulfoxy substituents, etc. The same substituents used to enhance solubility may also be present on $Y_1$, $Y_2$ or X. Ar is an aryl moiety, typically phenyl or naphthyl, most preferably phenyl. Z is a moiety that includes a bond that is cleaved by an enzyme, which, when cleaved, leaves either O or N attached to the aryl moiety. This anion destabilizes the dioxetane, leading to its decomposition. On decomposition, the dioxetane releases light. For the purposes of this invention, Z is a phosphate moiety, preferably disodium phosphate.

Dioxetanes of this type are disclosed in U.S. Pat. Nos. 4,962,192; 4,931,569; 5,112,960; 5,145,772 and 5,654,154. All of the foregoing patents are incorporated herein by reference in their entirety. As disclosed, for example, in U.S. Pat. No. 5,112,960, an enzyme-triggerable dioxetane such as 3-(4-methoxyspiro[1,2-dioxetane-3, 2'-tricyclo[3.3.1.1$^{3.7}$] decan]-4yl)-phenyl phosphate and its salts is a highly effective reporter molecule of this type. This dioxetane is commercially available as "AMPPD", which is a registered trademark of Applera Corporation or its subsidiaries. Derivitization of this "unsubstituted" 1,2-dioxetane with substituents on the adamantyl ring, such as a chlorine atom, can dramatically improve performance. A chlorine substituted dioxetane is commercially available as "CSPD", which is a registered trademark of Applera Corporation or its subsidiaries. Similarly, substituents on the phenyl ring besides the enzyme-cleavable substituent, particularly at the 3 or meta position, give further improved yields. These reporter molecules, which are chemiluminescent in nature, are referred to as enzyme-triggerable dioxetanes. The particular enzyme preferably acting in the claimed invention is alkaline phosphatase selecting, therefore, Z as a phosphate moiety.

As set forth in U.S. Pat. No. 5,145,772 and U.S. Pat. No. 5,336,595, both of which are also incorporated herein by reference, the use of polymeric onium salts (e.g., ammonium, phosphonium and sulfonium) as enhancer molecules results in a heightened degree of light emission from the dioxetane on decomposition. This is because of the tendency of these macromolecular polymers to sequester the dioxetane anion, which is highly hydrophobic in non-aqueous "micro-environments," which can maximize chemiluminescent emissions. The 1,2-dioxetanes can also be used with secondary enhancement agents such as those taught in U.S. Pat. No. 5,547,836, which is also incorporated by reference in its entirety.

As further disclosed in U.S. Pat. No. 5,145,772, these dioxetanes may be combined with energy accepting fluorescent molecules, such as fluorescein, such that the energy released by the dioxetane on decomposition is transferred to the fluorescent receiver, with the fluorescence being detected. The assay of this invention is particularly suited for chemiluminescent emission.

In the assay of the present invention, a well (e.g., a micro-well) of an assay plate or similar reaction chamber is coated with a capture antibody. According to the invention, cell growth, induction and lysis can all take place in the antibody-coated wells of the assay plate. Subsequently, a conjugate of an analyte (e.g., a cyclic nucleotide such as cAMP) and an enzyme (e.g., alkaline phosphatase) can be added to the wells, along with an antibody for the analyte, to form a reaction mixture. The reaction mixture can then be incubated and washed. Thereafter, a substrate (e.g., a 1,2- dioxetane substrate) which is triggered by the enzyme of the conjugate can be added. When the substrate is a 1,2-dioxetane, a chemiluminescent enhancing agent such as poly(vinylbenzyltributyl ammonium chloride) is also preferably added to the wells. The substrate is then incubated, and the reaction chamber inspected, preferably with a luminometer or some other type of light-sensitive device (e.g., a CCD), for a signal. The strength of the signal is an indication of the concentration of analyte in the sample. For example, the stronger the signal, the lower the analyte concentration in the sample.

The present inventors have found that, surprisingly, antibody on an assay plate (i.e., the capture antibody) retains its ability to bind a primary antibody after cells are grown on the same plate. Therefore, according to the invention, the cells can be grown, induced, lysed and assayed on the same plate. In this manner, the conventional step of transferring sample from a tissue culture plate on which the cells are grown, induced, and lysed to a second assay plate for screening can be eliminated. As a result, the assay according to the invention requires fewer steps and is therefore easier to automate and less expensive to run.

The assay protocol of the present invention is a competitive assay in which the intracellular analyte and the conjugate compete for binding sites on the sample plate. Therefore, there is an inverse relationship between the intensity of the signal detected and the concentration of the analyte in the sample.

The assay of the present invention is generically applicable to all immunoassays, but is particularly applicable to assays for cyclic nucleotides, including cAMP, cGMP, cCMP, cUMP, cIMP and cTMP. Among the cyclic nucleotides, cAMP is perhaps the most widely known and is implicated as a primary or secondary messenger in a variety of cellular, intracellular and extracellular pathways. Frequently, cAMP and cGMP appear in a tandem, inverse relationship in a wide variety of biophysical pathways; therefore, cAMP and cGMP receive the most attention. cAMP, however, is clearly the most well studied and characterized of the cyclic nucleotides. The following description of the present invention, therefore, is exemplified using cAMP and cAMP detection reagents. The substitution of reagents, in particular, primary antibodies, preferably monoclonal antibodies, for the other cyclic nucleotides is straight forward and easily arrived at by one of skill in the art, given the disclosure herein.

Although cyclic nucleotides such as cAMP are exemplified above, any cell-based analyte can be assayed according to the invention. For example, cytokines and chemokines can also be assayed according to the invention.

The present invention is also exemplified using, as a substrate, a chlorine substituted dioxetane where, in the general Formula I given above, the adamantyl group is substituted with one chlorine atom, X is hydrogen, R is methyl and Z is phosphate. However, any substrate which gives off a signal when triggered by an enzyme can be used according to the invention. Suitable substrates include chemiluminescent, fluorescent and calorimetric substrates. For example, when the substrate is a 1,2-dioxetane, any enzyme-triggerable 1,2-dioxetane complex corresponding to the general Formula I may be used according to the invention. The enzyme of the conjugate can be any enzyme which triggers the substrate being used including, but not limited to alkaline phosphatase. Thus, a conjugate of the analyte and any exogenous substrate can be used in the present invention.

According to the present invention, an enhancement agent for enhancing chemiluminescent emissions can be used. Such a material is commercially available from Applied Biosystems. As an exemplary enhancement agent, poly (vinylbenzyltributylammonium chloride) can be used. An enhancement agent is preferred, but is not required for the practice of the invention. Other quaternary onium polymers, as well as hydrophobic macromolecules such as large proteins, including bovine serum albumin or mixtures thereof, may be similarly employed.

Although enzyme conjugates are discussed above, any tagged analyte can be used according to the invention. For example, an analyte having a radioactive or fluorescent tag can be used to compete with intracellular analyte for binding sites on the assay plate. After washing, the amount of fluorescent or radioactive tagged material on the plate can then be determined using conventional assay techniques.

In current, conventional assay protocols, cells are grown and induced in a tissue culture plate and the cell lysate is transferred to a separate assay plate for determination of cAMP or other intracellular analyte levels. According to the present invention, cell growth, cell induction, cell lysis and determination of intracellular analyte levels in cell-based heterogeneous assays can all be performed in the wells of the same antibody-coated assay plate. As used herein, the term "cell-based" refers to assays, like the present invention, that measure the response of a cell to a stimulus and, more specifically, the response of a cell to a stimulus in terms of production of a cyclic nucleotide phosphate such as cAMP.

In the practice of the present invention, the wells of conventional microplates, or similar reaction chambers, are first coated with a capture antibody. The plates are preferably microplates having optically transparent well bottoms so that cell growth and lysis therein may be visualized. In the exemplification of the invention, the capture antibody is a goat anti-rabbit antibody, such as that available from American Qualex. The wells of the plates are coated with a preparation of the capture antibody, incubated overnight and then washed. To avoid non-specific binding, the rest of the plate may be treated so as to suppress any interaction therewith. After washing, each plate is treated with SUPER-BLOCK® blocking buffer (available from Pierce) or a similar agent. The plate is then dried. This process is illustrated in FIG. 1.

The prepared plates are now ready to be used as reaction chambers, or wells, for the competitive assay. The source of cAMP may be either standards prepared to specific dilutions, in order to establish standardized values, or cells that have been subjected to some type of stimulus and then lysed so as to provide sample material for inspection. Cells are added to the wells wherein cell growth, cell induction and cell lysis then take place. To perform the assay, a conjugate of cAMP and alkaline phosphatase, described herein below, is added to the well to form a reaction mixture with the lysed cells therein. The final addition to the reaction mixture is the primary antibody (e.g., an antibody for cAMP). Both polyclonal and monoclonal antibodies are available against cAMP. Either may be used effectively. Rabbit anti-cAMP antibodies are available from Zymed Laboratories, Inc., as well as from Immunogen. Other antibodies are similarly available. The reactants are mixed in the coated well and then incubated, preferably overnight, to insure adequate antibody binding. Subsequently, the incubated reaction mixture is washed repeatedly with a wash buffer, which may be, for example, 0.05 M carbonate bicarbonate and 0.05% surfactant, preferably polysorbate 20 (available from ICI Surfactants under the trademark Tween-20®), at a pH of about 8.0–11.0, an exemplary value being about 9.6. While not wishing to be bound by this theory, it appears that the alkaline character of the wash buffer may improve alkaline phosphatase performance. The assay buffer itself comprises BSA (0.02%) with sodium acetate (0.05 molar) at a pH convenient for the assay, between about 5.5 and 6.0, preferably about 5.8. Those of skill in the art will appreciate that the identities of the blocking buffer, the wash buffer and the assay buffer, as well as the buffer used to coat the microwells, are not rigid features of the invention, per se, but rather can be varied by those of ordinary skill in the art and still employ the claimed invention.

After washing, the dioxetane, along with the enhancer, if any, is added. A further incubation to permit a glow discharge from the chemiluminescent dioxetane to reach a constant level, approximately 30 minutes at room temperature, follows and then the chemiluminescent signal is read in a detection device. Suitable detection devices include the TR717™ microplate luminometer or the NorthStar™ HTS Workstation. TR717™ and NorthStar™ are trademarks of Applera Corporation and its subsidiaries.

It is clear that the assay is optimized for automated robotic assay systems, providing high throughput opportunities. Results, in terms of sensitivity and dynamic range can be significantly improved if the microplates, or other reaction chambers, are shaken during the incubation period. The relative performance of shaken and non-shaken assays is reflected in FIGS. 2A and 2B.

Figure 2A:
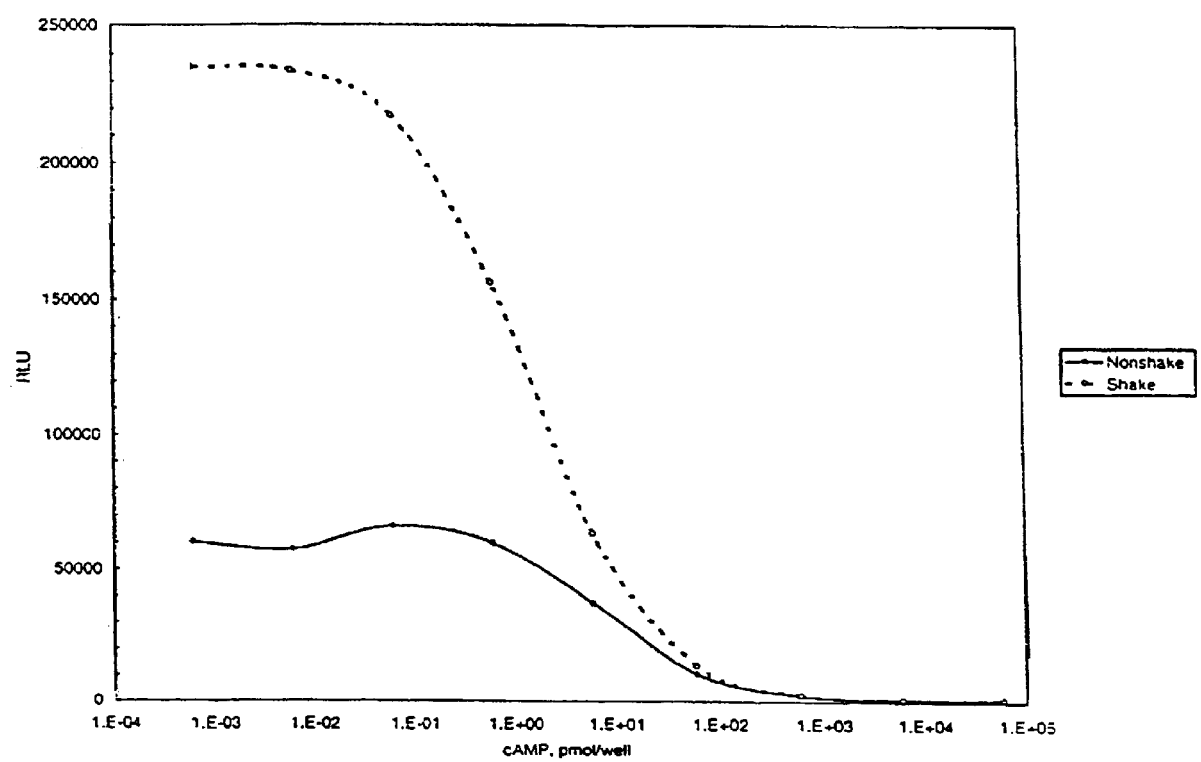

In FIG. 2A, light intensity is plotted as a function of cAMP concentration in pmol/well for both a shaken (○) and a non-shaken (●) assay. The data in FIG. 2A was taken for a one hour incubation time. The data for the experiment is tabulated in FIG. 2B along with calculated values of signal to noise ratio at each concentration evaluated. As can be seen from FIGS. 2A and 2B, the shaken assays provide significantly higher resolution, particularly at lower cAMP concentrations.

This assay is suitable for use in a wide variety of conditions. The heightened sensitivity, as well as the broadened dynamic range, makes application consistent with a wide variety of variables. When standards have been established, the samples assayed according to this invention can be obtained by lysing mammalian adherent and non-adherent cell lines. Optimal performance can be achieved across a wide range of cell densities, ranging from 1,000–100,000 cells per well, depending on cell type in a 96-well plate. Other plates with a higher number of wells may be used. Luminometers can be used to detect the chemiluminescent signal (i.e., light emission) according to the invention. If a luminometer is used, then an appropriate measure is about one second per well. In the alternative, a scintillation counter such as that available under the trademark TOP COUNT® may be used as a substitute for a luminometer. Sensitivity may be reduced, and it may be necessary to turn off the coincident circuit to measure chemiluminescence directly.

The "competitive" basis of the assay is the use of a conjugate of an analyte (e.g., cAMP) and an enzyme such as alkaline phosphatase (e.g., cAMP-AP conjugate) to compete with analyte in the sample for antibody. It is the enzyme of the analyte-enzyme conjugate, captured by the antibody specific for the analyte, that cleaves the enzyme-cleavable dioxetane to produce the signal. Therefore, the lower the analyte concentration in the lysed sample, the more of the analyte-enzyme conjugate will be captured by the primary antibody, and the larger the resulting signal will be.

Figure 3:
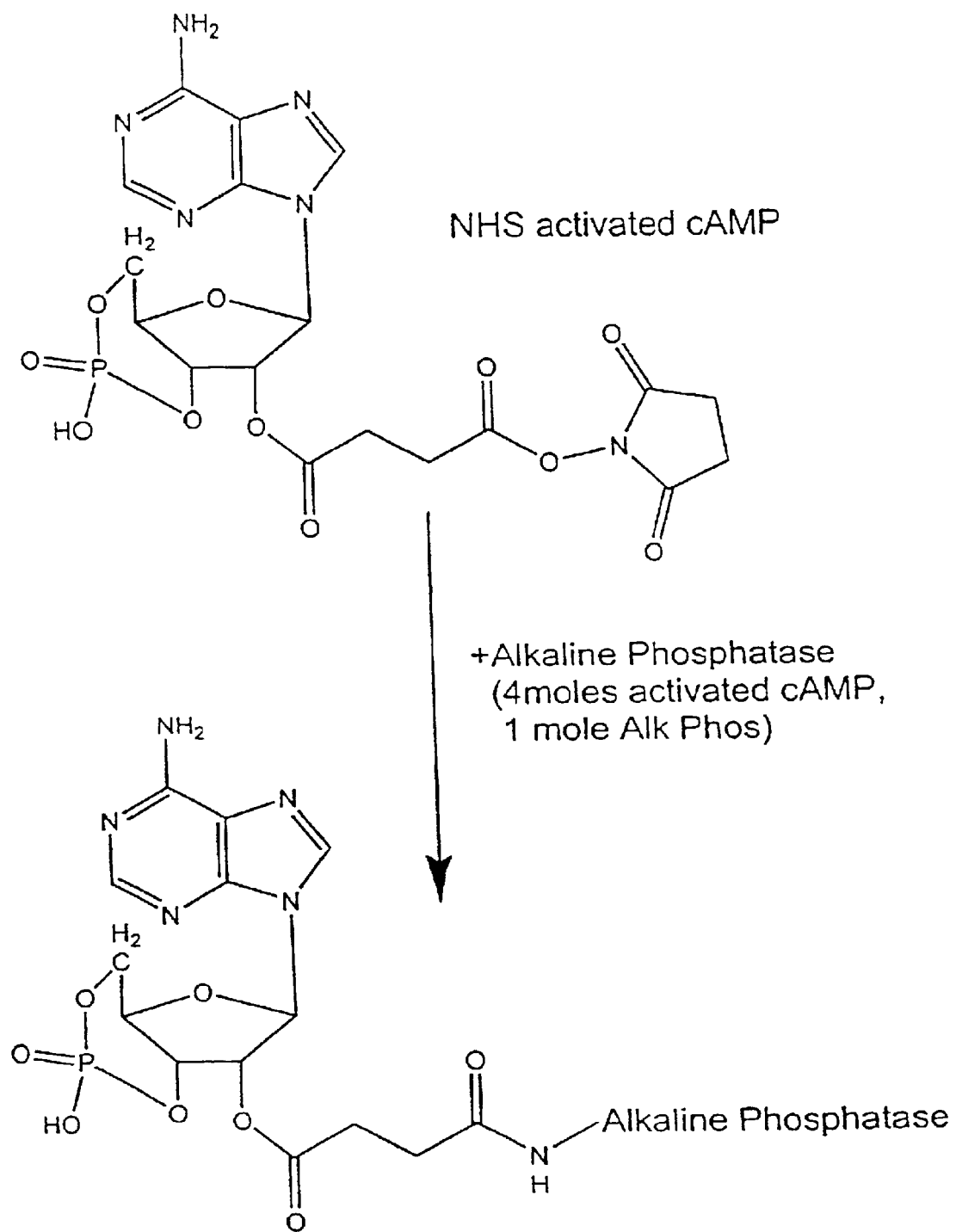
FIG. 3 is a schematic illustration of the formation of the alkaline phosphatase/cyclic nucleotide conjugate of the invention.

The synthesis of an analyte-enzyme conjugate according to the invention is illustrated in FIG. 3. As shown in FIG. 3, a cAMP-AP conjugate can be prepared by combining NHS activated cAMP with alkaline phosphatase in a ratio of 4 moles activated cAMP to 1 mole AP. Other analyte-enzyme conjugates can also be prepared using synthetic chemical techniques known in the art.

Figure 4:
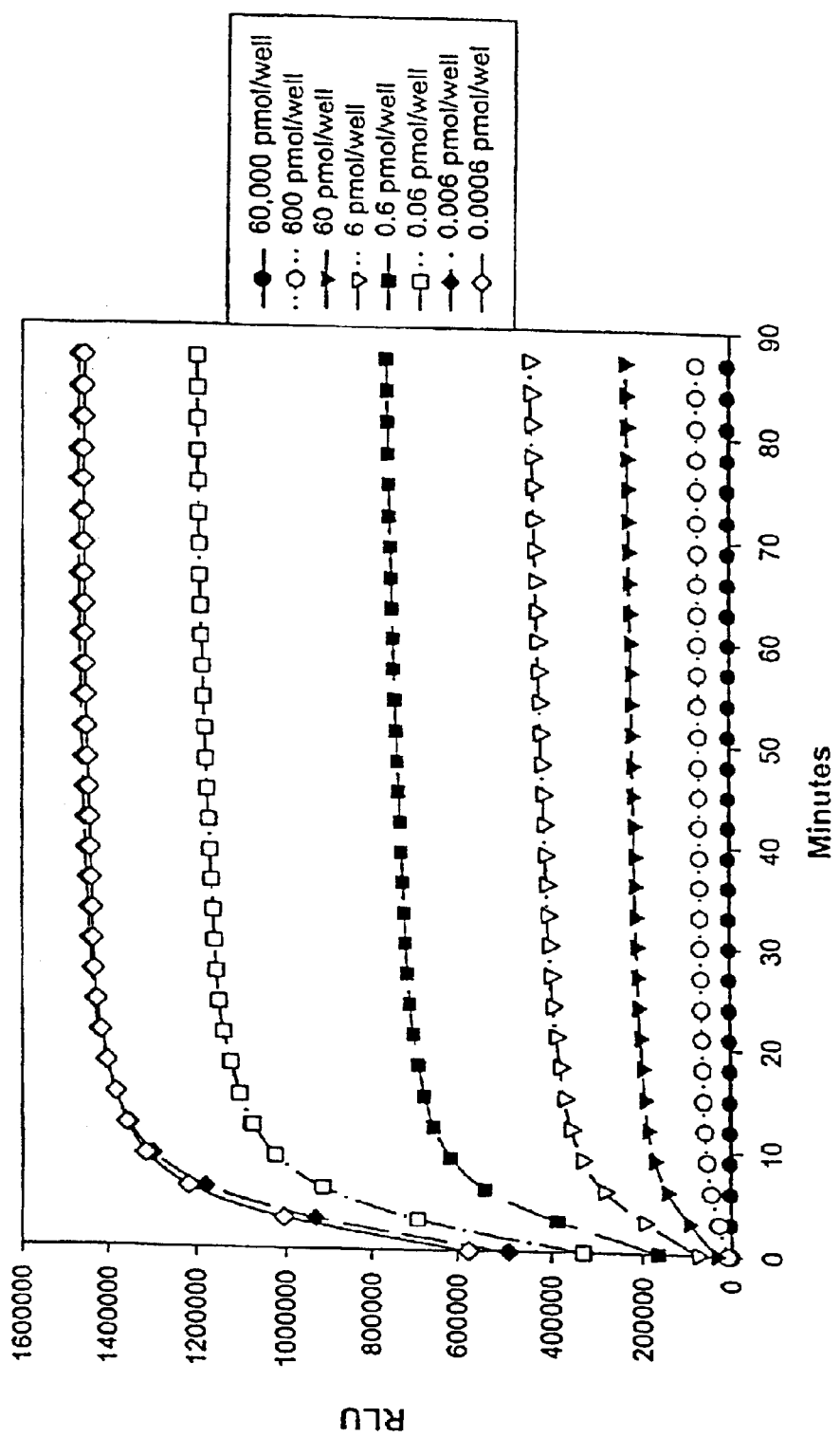
FIG. 4 is a graphic illustration of standardized signals vs. time for a variety of concentrations of cAMP.

As noted above, it may be desirable to establish standards so that actual concentrations in lysed samples can be determined on the basis of established concentration. A typical standard curve collection is shown in FIG. 4 which is a graph showing luminescence (RLU) as a function of time (minutes) for various cAMP concentrations.

Sensitivity and dynamic range for a variety of cAMP detection assays have been published. The sensitivity and dynamic range for various detection systems including the chemiluminescent ELISA system according to the invention are presented in FIG. 5. It is clear from the data in FIG. 5 that the improvements in sensitivity and dynamic range obtained by combining dioxetane chemiluminescent technology with cAMP-specific immunoassay techniques has led to an unexpectedly superior performance, even in the absence of acetylation.

Figure 6A:
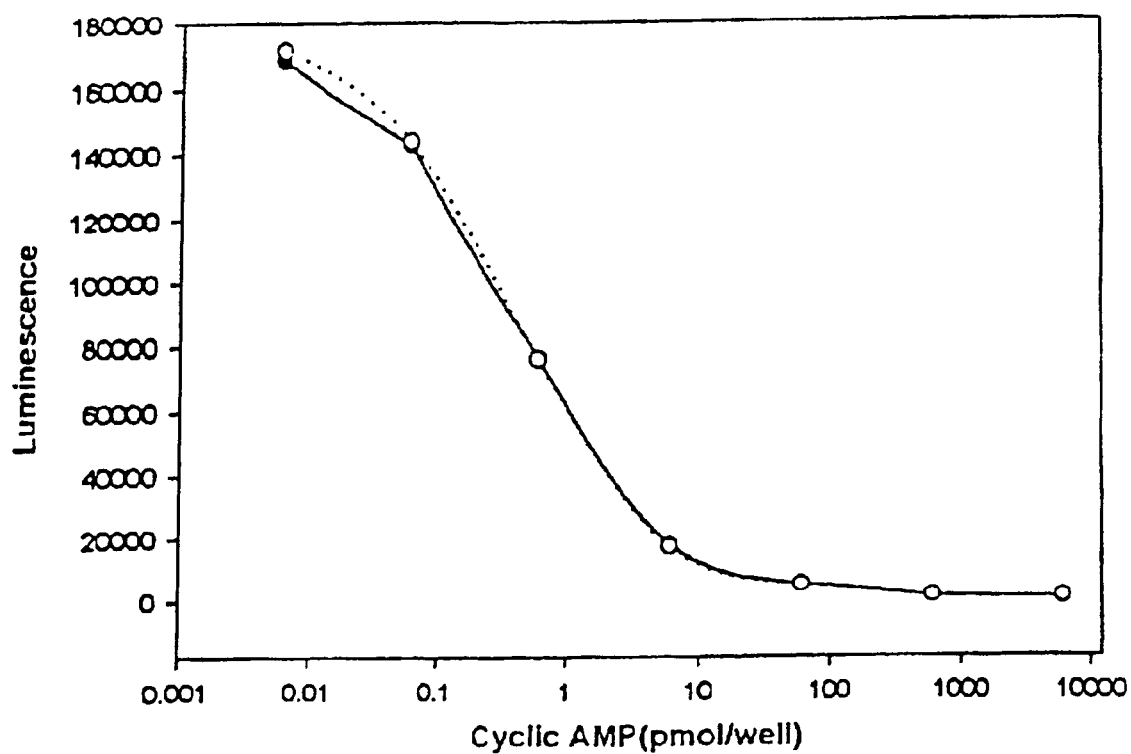

As previously noted, light emissions according to the invention are preferably detected using a luminometer or a charge coupled device (CCD). Two exemplary detection devices, a TR717™ microplate luminometer and a NorthStar™ HTS Workstation, are compared in FIG. 6. In FIG. 6A, luminescence is plotted as a function of cAMP concentration (pmol/well) for the TR717™ microplate luminometer (●) at 1 second/well read and a NorthStar™ HTS Workstation (○) at 1 minute/plate read. In FIG. 6B, the data for the experiments are tabulated and the signal to noise ratios are calculated for each cAMP concentration measured. As can be seen from the data in FIGS. 6A and 6B, both devices give improved performance advantangeously provided by this invention.

The ability to perform all steps of a cell-based heterogeneous assay in an antibody-coated microplate has several advantages. First, the removal of a step from the assay, e.g., the transfer step, makes automation of the assay easier to perform and improves coefficients of variation. Next, the ability to have a more concentrated cell lysate as a void volume for the transfer step is no longer a concern. This will be especially advantageous in situations where small amounts of sample are being measured. Also, eliminating the necessity of a second plate, e.g., the tissue culture plate, decreases the cost of performing the assay.

The invention will now be described by reference to the following detailed examples. The examples are set forth by way of illustration and are not intended to be limiting in scope.

EXAMPLES

Present Invention

According to the present invention, adherent SK-N-MC cells are grown in a T-225 flask and dissociated using an enzyme-free solution (C-1544) available from Sigma. Cells are counted at 90,000/ml and seeded in both a 96-well, clear-bottom, antibody-coated plate (90 µl/well, or 8,100 cells/well) and a 384-well, clear-bottom, antibody-coated plate (50 µl/well, or 4,500 cells/well). Cells are allowed to adhere for about 90 hours before removing the media using a plate washer. Fresh media is added with 0.5% FBS and 1 mM IBMX (from a 500 mM stock, final percent DMSO is 0.20%) at 80 µl/well for 96-well plates and 40 µl/well for 384-well plates. Cells are about 80% confluent and are not removed upon media aspiration. Plates are allowed to equilibrate for about half an hour at about 37° C. in 5% $CO_2$ before agonist additions.

Addition #1 ($G_i$-agonist): Human Neuropeptide Y (NPY) diluted in HEPES is added to the plates (10 μl/well for 96-well plates and 5 μl/well for 384-well plates) at the following final concentrations: 0, 1, 10 and 100 nM. The NPY is incubated for about half an hour at about 37° C. in 5% $CO_2$ before the second addition.

Addition #2 ($G_S$-agonist/forskolin): Isoproterenol and forskolin are diluted in HEPES and added to the plates (10 μl/well for 96-well plates and 5 μl/well for 384-well plates) at the following final concentrations: 0, 1, 10 and 100 μM. The isoproterenol and forskolin are incubated for about half an hour at about 37° C. in 5% $CO_2$ before cell lysis.

Cell lysis: Media and agonists are removed using a plate washer. Assay/lysis buffer is added to the plates (60 μl/well for 96-well plates and 20 μl/well for 384-well plates) and allowed to lyse for about half an hour at about 37° C. Cell lysis is confirmed using a microscope.

cAMP assay: cAMP-AP conjugate is added to the plates (30 μl/well for 96-well plates and 10 μl/well for 384-well plates), followed by the addition of cAMP antibody to the plates (60 μl/well for 96-well plates and 20 μl/well for 384-well plates). The plates are sealed and incubated overnight. After incubation, the plates are washed with cAMP wash buffer using a plate washer. CSPD® substrate with Sapphire-II™ enhancer is then added to the plates (100 μl/well for 96-well plates and 30 μl/well for 384-well plates) and allowed to incubate at room temperature for about half an hour before reading on the TR717™ microplate luminometer and NorthStar™ HTS Workstation. The data is presented in FIGS. 7A, 7B and 7C.

The standard curve data for the 384-well plate is set forth below in TABLE I.

mM IBMX (from a 500 mM stock, final percent DMSO is 0.20%) at 80 μl/well for 96-well plates and 40 μl/well for 384-well plates. Cells are about 95% confluent and are not removed upon media aspiration. Plates are allowed to equilibrate for about half an hour at about 37° C. in 5% $CO_2$ before agonist additions.

Addition #1 ($G_i$-agonist): Human Neuropeptide Y (NPY) diluted in HEPES is added to the plates (10 μl/well for 96-well plates and 5 μl/well for 384-well plates) at the following final concentrations: 0, 1, 10 and 100 nM. The NPY is incubated for about half an hour at about 37° C. in 5% $CO_2$ before the second addition.

Addition #2 ($G_S$-agonist/forskolin): Isoproterenol and forskolin are diluted in HEPES and added to the plates (10 μl/well for 96-well plates and 5 μl/well for 384-well plates) at the following final concentrations: 0, 1, 10 and 100 μM. The isoproterenol and forskolin are incubated for about half an hour at about 37° C. in 5% $CO_2$ before cell lysis.

Cell lysis: Media and agonists are removed using a plate washer. Assay/lysis buffer is added to the plates (100 μl/well for 96-well plates and 40 μl/well for 384-well plates) and allowed to lyse for about half an hour at about 37° C. Cell lysis is confirmed using a microscope.

cAMP assay: Cell lysate is transferred to assay capture plates (60 μl/well for 96-well plates and 20 μl/well for 384-well plates), followed by addition of cAMP-AP conjugate (30 μl/well for 96-well plates and 10 μl/well for 384-well plates). cAMP antibody is then added to the plates (60 μl/well for 96-well plates and 20 μl/well for 384-well plates). The plates are sealed and incubated overnight. After incubation, the plates are washed with cAMP wash buffer using a plate washer. CSPD® substrate with Sapphire-II™

TABLE I

Standard Curve

| pmol/well | | 3 | 4 | 5 | 6 | Average | SD | % CV |
|---|---|---|---|---|---|---|---|---|
| 0 | A | 92206 | 84916 | 84835 | 82509 | 83396.75 | 4322 | 5% |
| 0 | B | 82973 | 80699 | 81806 | 77230 | | | |
| 0.02 | C | 78966 | 76130 | 75390 | 69371 | 72896 | 5094 | 7% |
| 0.02 | D | 78869 | 71011 | 66540 | 66888 | | | |
| 0.2 | E | 65816 | 60471 | 62994 | 47290 | 57992 | 6505 | 11% |
| 0.2 | F | 51961 | 63379 | 58845 | 53179 | | | |
| 2 | G | 28490 | 28243 | 32744 | 27672 | 29983 | 1795 | 6% |
| 2 | H | 31772 | 30205 | 31103 | 28637 | | | |
| 20 | I | 8904 | 9105 | 9301 | 9053 | 8868 | 354 | 4% |
| 20 | J | 8997 | 8758 | 8692 | 8134 | | | |
| 200 | K | 1970 | 2032 | 2062 | 1873 | 1843 | 161 | 9% |
| 200 | L | 1681 | 1711 | 1698 | 1716 | | | |
| 2,000 | M | 696 | 701 | 700 | 676 | 682.875 | 15 | 2% |
| 2,000 | N | 664 | 665 | 688 | 673 | | | |
| | | | | | Ratio | S/N | | |
| | | | | | 0/0.02 | 1.14 | 0.694684 | |
| | | | | | 0/0.2 | 1.44 | | |
| | | | | | 0/2,000 | 122 | | |

Comparative Example

According to a current, conventional cAMP assay protocol, adherent SK-N-MC cells are grown in a T-225 flask and dissociated using an enzyme-free solution (C-1544) available from Sigma. Cells are counted at 90,000/ml and seeded in both a 96-well tissue culture plate (90 μl/well, or 8,100 cells/well) and a 384-well tissue culture plate (50 μl/well, or 4,500 cells/well). Cells are allowed to adhere for about 90 hours before removing the media using a plate washer. Fresh media is added with 0.5% FBS and 1 enhancer is then added to the plates (100 μl/well for 96-well plates and 30 μl/well for 384-well plates) and allowed to incubate at room temperature for about half an hour before reading on the TR717™ microplate luminometer and NorthStar™ HTS Workstation. The data is presented in FIG. 8.

The standard curve data for the 384-well plate of this example is set forth below in TABLE II.

TABLE II

Standard Curve

| pmol/well | | 3 | 4 | 5 | 6 | Average | SD | % CV |
|---|---|---|---|---|---|---|---|---|
| 0 | A | 86534 | 100456 | 86903 | 103785 | 96572 | 6849 | 7% |
| 0 | B | 97089 | 102159 | 101846 | 93804 | | | |
| 0.02 | C | 81611 | 93441 | 78408 | 71975 | 74076 | 11750 | 16% |
| 0.02 | D | 80571 | 56760 | 65879 | 63966 | | | |
| 0.2 | E | 42777 | 56213 | 44729 | 54845 | 48348 | 5061 | 10% |
| 0.2 | F | 49171 | 42896 | 48588 | 47562 | | | |
| 2 | G | 18007 | 21083 | 16483 | 23789 | 20174 | 3240 | 16% |
| 2 | H | 15323 | 22366 | 20593 | 23744 | | | |
| 20 | I | 4783 | 6068 | 5179 | 4911 | 5429 | 860 | 16% |
| 20 | J | 5244 | 5375 | 7252 | 4616 | | | |
| 200 | K | 1592 | 1822 | 1825 | 1563 | 1802 | 157 | 9% |
| 200 | L | 2000 | 1822 | 1980 | 1813 | | | |
| 2,000 | M | 777 | 811 | 715 | 742 | 783 | 46 | 6% |
| 2,000 | N | 826 | 851 | 793 | 749 | | | |

| | Ratio | S/N |
|---|---|---|
| | 0/0.02 | 1.30 |
| | 0/0.2 | 2.00 |
| | 0/2,000 | 123 |

The data shows that the present invention improves the performance characteristics of cell-based, ELISA-type assays. The coefficient of variation (% CV) achieved with the assay of the present invention has improved. The observed improvement may have resulted from the elimination of the transfer step. The elimination of this step may also eliminate any associated pipetting error. Moreover, the signal to noise ratio (S/N) between basal and stimulated cells may have increased since removal of the transfer step allows the entire cell lysate to be used in the assay and, therefore, higher levels of cAMP can be measured.

The above data suggests that there is no detrimental effect in growing cells on top of the antibody-coated microplate surface in relationship to the antibody's ability to perform the assay. Rather, as shown by the above findings, cells grown on the antibody-coated microplate maintain their ability to be induced to stimulate or inhibit cAMP production.

Figure 9A:
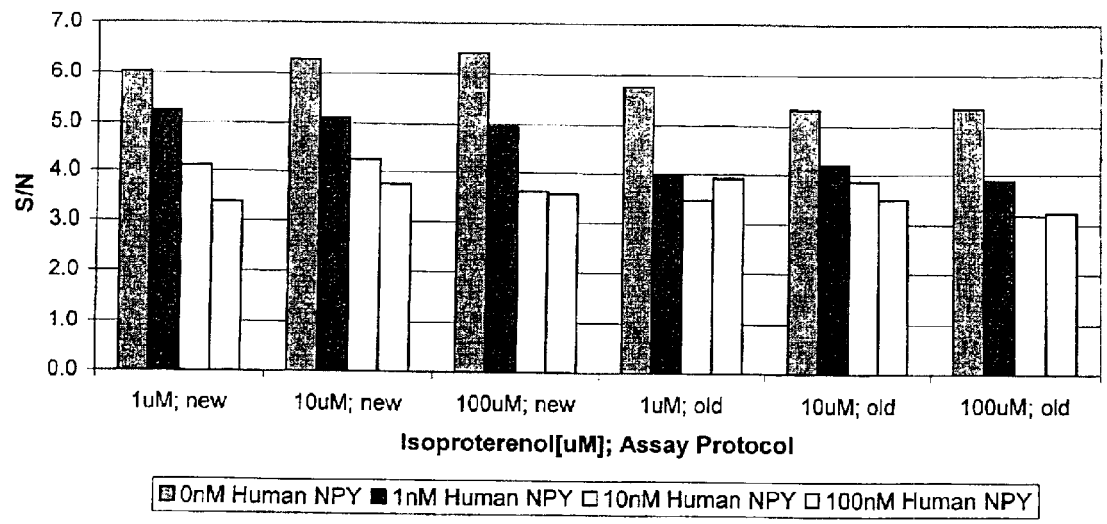
FIG. 9 is a graph comparing the stimulation/inhibition of cAMP production in SK-N-MC cells in both an assay according to the present invention and a conventional assay.
Figure 9B:
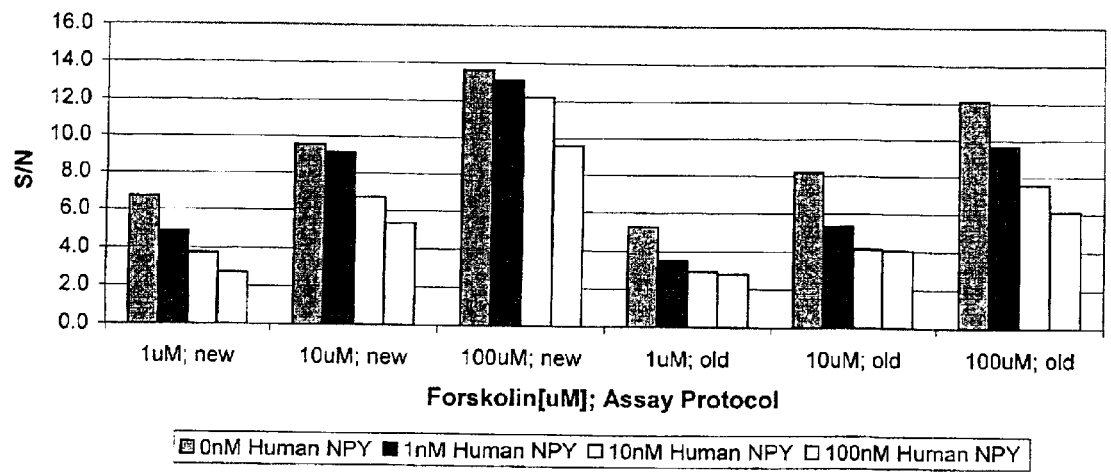

FIGS. 9A and 9B are bar charts comparing the stimulation/inhibition of cAMP production in SK-N-MC cells in an assay according to the present invention and in a conventional assay. FIG. 9A shows data for a 384-well cAMP-Screen™ assay protocol for four different human neuropeptide Y (NPY) concentrations (0, 1, 10 and 100 nM) and various isoproterenol concentrations (1, 10, and 100 µm). FIG. 9B shows data for a 384-well cAMP-Screen™ assay protocol for four different human neuropeptide Y (NPY) concentrations (0, 1, 10 and 100 nM) and various forskolin concentrations (1, 10, and 100 µm).

In FIGS. 9A and 9B, "new" refers to the protocol where the SK-N-MC cells are grown for four days, treated with agonists, lysed, and assayed all in the wells of a 384-well clear bottom assay capture plate. "Old" refers to the conventional protocol wherein the SK-N-MC cells are grown for four days, treated with agonists, and lysed, in a standard 384-well tissue culture plate. Cell lysate is then transferred to a 384-well solid-bottom assay capture plate for the cAMP assay.

The present invention is also directed to kits for conducting chemiluminescent assays to determine the amount of analyte in a sample comprising cells. According to the invention, the kit can comprise: an assay plate comprising one or more wells, wherein the wells are coated with a capture antibody; a conjugate of the analyte and an enzyme; a primary antibody that is bound by the capture antibody and that binds, when so bound, the analyte; a substrate which, when contacted with the enzyme in the conjugate, decomposes and releases light. The substrate can be a fluorescent, a chemiluminescent or a calorimetric substrate. According to a preferred embodiment of the invention, the substrate is a 1,2-dioxetane substrate. The enzyme according to the invention is preferably alkaline phosphatase.

According to a further embodiment of the invention, the analyte can be a cyclic nucleotide phosphate such as cyclic adenosine monophosphate (cAMP), cyclic guanosine monophosphate (cGMP), cyclic uridine monophosphate (cUMP) and cyclic cytidine monophosphate (cCMP). According to a preferred embodiment of the invention, the analyte is cyclic adenosine monophosphate (cAMP).

When the substrate is a 1,2-dioxetane, the kit can further comprise a chemiluminescent enhancing agent which enhances the amount of light emitted by the dioxetane when triggered in comparison with the amount of light emitted in the absence of the enhancer. According to a preferred embodiment of the invention, the chemiluminescent enhancing agent is a polymeric onium salt.

This invention has been disclosed generically and in terms of specific examples. The specific examples are not intended, and should not be construed, as limiting unless so indicated. In particular, variations in the identity of the dioxetane, buffer compositions, signal detecting apparatus, protocol time, temperatures and conditions and the like will occur to those of ordinary skill in the art without the exercise of inventive faculty. Unless excluded by the recitation of the claims set forth below, these variations remain within the scope of the invention.

What is claimed is:

1. A competitive immunoassay for detecting the amount of an analyte in a sample comprising cells, the immunoassay comprising steps of:

providing an assay plate comprising one or more wells, wherein the wells are coated with a capture antibody;

adding the sample to the one or more wells;

growing the cells of the sample in the one or more wells;

lysing the cells in the one or more wells;

combining with the cell lysates, or sample in the one or more wells, (1) a conjugate of the analyte and an enzyme and (2) a primary antibody that is bound by the capture antibody and that binds, when so bound, the analyte to form a reaction mixture;

incubating the reaction mixture to permit binding of the primary antibody and the conjugate;

washing the reaction mixture to remove unbound conjugate or antibody;

adding to the reaction mixture in the one or more wells a substrate comprising an enzyme labile group, wherein the enzyme of the conjugate is capable of cleaving the enzyme labile group of the substrate; and measuring a signal resulting from the cleavage of the enzyme labile group;

wherein the measured signal can be used to determine the presence and/or the concentration of the analyte in the sample.

2. The competitive assay of claim 1, wherein the analyte is a cyclic nucleotide phosphate.

3. The competitive assay of claim 2, wherein the analyte is selected from the group consisting of cyclic adenosine monophosphate (cAMP), cyclic guanosine monophosphate (cGMP), cyclic uridine monophosphate (cUMP) and cyclic cytidine monophosphate (cCMP).

4. The assay of claim 3, wherein the cyclic nucleotide phosphate is cyclic adenosine monophosphate (cAMP).

5. The assay of claim 4, wherein the cyclic adenosine monophosphate is acetylated or non-acetylated.

6. The assay of claim 5, wherein the cyclic adenosine monophosphate is non-acetylated and the sensitivity of the assay is about 0.005 pmol/well or less.

7. The assay of claim 5, wherein the cyclic adenosine monophosphate is non-acetylated and the assay has a dynamic range of about five logs or greater.

8. The assay of claim 1, wherein the enzyme is alkaline phosphatase.

9. The assay of claim 1, wherein the substrate is a chemiluminescent substrate, a fluorescent substrate or a colorimetric substrate.

10. The assay of claim 1, wherein the substrate is a 1,2-dioxetane.

11. The assay of claim 1, wherein the capture antibody is provided on a surface of the one or more wells.

12. The assay of claim 10, further comprising a step of adding a polymeric onium salt to the reaction mixture in the one or more wells, wherein the polymeric onium salt enhances the amount of light emitted by the dioxetane when triggered in comparison with the amount of light emitted in the absence of the enhancer.

13. The assay of claim 1, wherein the signal is detected by a luminometer or a charge coupled device (CCD).

14. The assay of claim 1, wherein the reaction mixture is shaken at least once during incubating.

15. The assay of claim 1, wherein the antibody that binds the analyte is a monoclonal antibody.

16. The assay of claim 1, wherein the washing step comprises washing with a buffer having a pH of 8.0 to 11.0.

17. The assay of claim 16, wherein the buffer comprises carbonate bicarbonate and a surfactant.

18. A competitive immunoassay for detecting the amount of a cyclic nucleotide phosphate in a sample comprising cells, the immunoassay comprising steps of:

providing an assay plate comprising one or more wells, wherein the wells are coated with a capture antibody;

adding the sample to the one or more wells;

growing the cells of the sample in the one or more wells;

lysing the cells in the one or more wells;

combining, with the cells in the one or more wells, (1) a conjugate of the cyclic nucleotide phosphate and an alkaline phosphatase and (2) a primary antibody that is bound by the capture antibody and that binds, when so bound, the cyclic nucleotide phosphate to form a reaction mixture;

incubating the reaction mixture to permit binding of the primary antibody and the conjugate;

washing the reaction mixture to remove unbound conjugate or antibody;

adding to the reaction mixture an alkaline phosphatase-triggered 1,2-dioxetane which, when contacted with the alkaline phosphatase of the conjugate, decomposes and releases light; and detecting light emitted by said reaction mixture;

wherein the light detected can be used to determine the presence and/or the concentration of the analyte in the sample.

19. The assay of claim 18, further comprising a step of adding a polymeric onium salt to the reaction mixture in the one or more wells, wherein the polymeric onium salt enhances the amount of light emitted by the dioxetane when triggered in comparison with the amount of light emitted in the absence of the enhancer.

20. A competitive immunoassay for detecting the amount of an analyte in a sample comprising cells, the immunoassay comprising steps of:

providing an assay plate comprising one or more wells, wherein the wells are coated with a capture antibody;

adding the sample to the one or more wells;

growing the cells of the sample in the one or more wells;

lysing the cells in the one or more wells;

combining with the cells in the one or more wells, (1) a tagged analyte and (2) a primary antibody that is bound by the capture antibody and that binds, when so bound, the analyte to form a reaction mixture;

incubating the reaction mixture to permit binding of the primary antibody and the tagged analyte;

washing the reaction mixture to remove unbound tagged analyte or antibody; and detecting a signal from the tagged analyte remaining in the one or more wells;

wherein the signal can be used to determine the presence and/or the concentration of the analyte in the sample.

21. The immunoassay of claim 20, wherein the analyte is tagged with a fluorescent or radioactive tag.

22. The assay of claim 1, wherein the cells adhere to a surface of the one or more wells.

* * * * *

UNITED STATES PATENT AND TRADEMARK OFFICE
CERTIFICATE OF CORRECTION

PATENT NO. : 6,794,156 B2
DATED : September 21, 2004
INVENTOR(S) : Anthony C. Chiulli It is certified that error appears in the above-identified patent and that said Letters Patent is hereby corrected as shown below:

Title page,
Item [57], ABSTRACT,
Lines 12-13, "calorimetric" should read -- colorimetric --.

Column 2,
Line 7, "$G_I$" should read -- $G_i$ --.
Line 50, "calorimetric" should read -- colorimetric --.

Column 5,
Line 59, "calorimetric" should read -- colorimetric --.

Column 9,
Line 1, "($G_I$-agonist):" should read -- ($G_i$-agonist): --.

Column 12,
Line 31, "calorimetric" should read -- colorimetric --.

Signed and Sealed this

Fifth Day of April, 2005

JON W. DUDAS
*Director of the United States Patent and Trademark Office*